United States Patent [19]

Corey

[11] Patent Number: 5,183,743
[45] Date of Patent: Feb. 2, 1993

[54] CHROMOGENIC DIBENZOXAZEPINONE AND DIBENZOTHIAZEPINONE ENZYME SUBSTRATES

[75] Inventor: Paul F. Corey, Elkhart, Ind.

[73] Assignee: Miles Inc., Elkhart, Ind.

[21] Appl. No.: 800,112

[22] Filed: Nov. 29, 1991

Related U.S. Application Data

[62] Division of Ser. No. 364,157, Jun. 12, 1989.

[51] Int. Cl.$^5$ .................. C12Q 1/54; C12Q 1/38; C12Q 1/00; C12Q 1/50
[52] U.S. Cl. .................. 435/18; 435/14; 435/22; 435/7.92; 435/23; 536/18.1
[58] Field of Search .............. 435/18, 14, 7.92, 22, 435/23; 536/18.1

[56] References Cited

U.S. PATENT DOCUMENTS

| | | | |
|---|---|---|---|
| Re. 31,006 | 8/1982 | Schuurs et al. | 435/7.92 |
| 4,321,364 | 3/1982 | McCleary | 536/18.1 |
| 4,517,287 | 5/1985 | Scheibe et al. | 435/14 |
| 4,716,222 | 12/1987 | Wallenfels et al. | 536/18.1 |
| 4,810,636 | 3/1989 | Corey | 435/14 |
| 4,932,871 | 6/1990 | Bell et al. | 435/22 |

OTHER PUBLICATIONS

Graan et al, "Analytical Biochemistry" (144); 193–198; (1985).

Primary Examiner—Ronald W. Griffin
Assistant Examiner—Louise Leary
Attorney, Agent, or Firm—Andrew L. Klawitter; Jerome L. Jeffers

[57] ABSTRACT

Chromogenic enzyme substrate compounds comprising a dibenz[b,e] [1,4]oxazepinone or dibenzo[b,e] [1,4]thiazepinone nucleus having an enzyme-cleavable group such as a radical of a sugar, carboxylic acid, amino acid, peptide, phosphoric acid, or sulfuric acid. The substrate compounds are, in general, highly soluble in aqueous media and only slightly colored, and produce, upon enzyme cleavage, a chromogen exhibiting a large change in absorbance and a pKa below 7. Such substrates find use as indicators for the determination of enzyme analytes and enzymes used as markers in a variety of assays, including immunoassays.

19 Claims, 4 Drawing Sheets

CHROMOGENIC DIBENZOXAZEPINONE AND DIBENZOTHIAZEPINONE ENZYME SUBSTRATES

This is a division of application Ser. No. 364,157, filed on Jun. 12, 1989, now allowed.

BACKGROUND OF THE INVENTION

The present invention relates to chromogenic compounds which are useful as optical indicator compounds in analytical test systems. In particular, the present invention relates to novel chromogenic enzyme substrate compounds and their use in analytical test systems for the detection of enzymes in a liquid test sample.

The determination of enzymes is important in a variety of fields such as biochemical research, environmental and industrial testing, and medical diagnostics. The quantitation of enzyme levels in body fluids such as serum and plasma provides very useful information to the physician in diagnosing diseased states and their treatment. In addition to being analytes of interest in biological fluids, enzymes can also serve as detection reagents in a variety of analytical systems such as immunoassays and nucleic acid hybridization techniques. In such systems, enzymes are useful either directly or indirectly as labels to monitor the extent of antigen-antibody binding or nucleic acid hybridization that occurs.

Accordingly, the desire to detect enzyme analytes and to use enzyme labels as a diagnostic tool in various analytical test systems has given rise to the development of optical indicator compounds for use in the detection and measurement of the activity of such enzymes. Typically, such known optical indicator compounds comprise a detectable chemical group, such as a fluorogen or a chromogen, which has been derivatized with an enzyme cleavable substrate group specific for the enzyme of interest. Such optical indicator compounds exhibit an optical signal which is different from the optical signal which is provided by the cleaved native form of the fluorogen or chromogen. In principle, the enzyme cleaves the indicator compound to liberate the fluorogen or chromogen in the form of a distinctly fluorescent or colored product to provide a change in fluorescence or color which is proportional to the amount of enzyme present which, in turn, can be correlated to the amount of analyte present in a liquid test sample.

In particular, the detection and/or determination of hydrolases, i.e., enzymes which catalyse hydrolysis reactions of esters, glycosidic bonds, peptide bonds, other carbon-nitrogen bonds, and acid anhydrides [see Lehninger, *Biochemistry* (Worth Publishers, Inc., New York, N.Y., 1970) p. 148], is of interest in the diagnosis and monitoring of various diseases such as, for example, the determination of amylase and lipase in the diagnosis of pancreatic dysfunction [see Kaplan and Pesce, *Clinical Chemistry—Theory, Analysis and Correlation* (C. V. Mosby Co., St. Louis, Mo., 1984) Chapter 56], determination of N-acetylglucosaminidase (NAG) as an indicator of renal disease [see Price, *Curr. Probl. Clin. Biochem.* 9, 150 (1979)], and detection of esterase as an indicator for leukocytes [see Skjold, *Clin. Chem.* 31, 993 (1985)]. Further to their value in disease monitoring, hydrolases in recent years have gained importance in the diagnostic as well as in the biotechnology areas. For example alkaline phosphatase and, preferably, $\beta$-D-galactosidase have found increasing use as indicator enzymes for enzyme immunoassays [see *Annals of Clinical Biochemistry* 16, 221-40 (1979)].

Accordingly, the use of enzymes such as glycosidases, particularly $\beta$-D-galactosidase, as indicator enzyme labels in analytical test systems has given rise to the development of substrate glycosides such as phenyl-$\beta$-D-galactoside, o-nitrophenyl-$\beta$-D-galactoside and p-nitrophenyl-$\beta$-D-galactoside [see *Biochem. Z.*, Vol. 333, p. 209 [1960)] which are hydrolysed by $\beta$-D-galactosidase to liberate the phenols which are determined photometrically in the ultraviolet range, or the nitrophenols which are determined in the shortwave visible range, respectively. European Patent Publication No. 156,347 and U.S. Pat. No. 4,810,636 describe glycosides of resorufin and acridinone derivatives, respectively, which are specific for and cleaved by the particular glycosidase of interest to liberate detectable chromogens. U.S. Pat. No. 3,950,322 describes an N-acylneuraminic acid derivatized with a fluorogen such as 4-methylumbelliferone, fluorescein, methylfluorescein, resorufin, or umbelliferone for the detection of neuraminidase where the fluorogenic substrate glycoside is similarly acted upon by the enzyme to liberate the fluorogen.

The use of $\beta$-D-galactosides has also been described in conjunction with histochemical investigations, such as the napthyl-$\beta$-D-galactosides described in *Histochemie*, Vol. 35, p. 199 and Vol. 37, p. 89 (1973), and the 6-bromo-$\alpha$-napthyl derivatives thereof described in *J. Biol. Chem.*, Vol. 195, p. 239 (1952). According to such test systems, the napthols which are liberated upon the interaction of the galactoside with the enzyme are reacted with various diazonium salts to yield the respective azo-dyes which can then be visualized.

Although such known optical indicator compounds are useful for the detection of enzyme analytes and labels in an analytical test system, a number of problems nevertheless exist which effect assay sensitivity and accuracy such as low extinction coefficients, poor water solubility, absorbance maxima which interfere with various pigments and other constituents commonly present in biological fluids, and color shifts between the optical indicator compound and the liberated chromogen or fluorogen which are difficult to measure without the use of complicated instruments.

Accordingly, it is an object of the present invention to provide chromogenic enzyme substrate compounds which can be employed as optical indicator compounds in analytical test systems for the accurate and sensitive determination of enzymes in a liquid test sample.

Further, it is an object of the present invention to provide chromogenic enzyme substrate compounds which can be incorporated into the solid, porous matrix of an analytical test device as optical indicator compounds for the measurement of enzymes incorporated therein or in a liquid test sample applied thereto.

SUMMARY OF THE INVENTION

The present invention provides novel chromogenic enzyme substrate compounds of the formula:

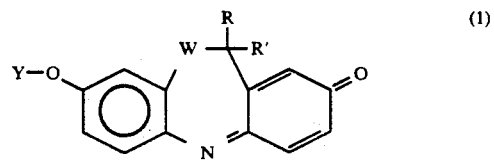

(1)

OR

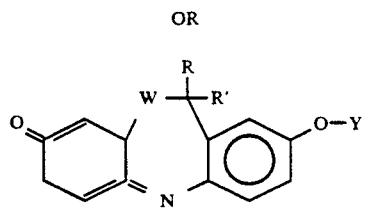

where Y represents an enzyme-cleavable group which is selected to confer specificity to a specific corresponding enzyme of analytical interest; W is oxygen or sulfur; and R and R', which can be the same or different, are hydrogen, alkyl, or aryl. The enzyme-cleavable group Y is a radical of a compound Y-OH comprising an enzyme-specific moiety which can be selected to confer specificity to any one of a wide variety of enzymes and includes, but is not necessarily limited to, enzyme-specific moieties such as sugars and derivatives thereof, acyl groups including aliphatic and aromatic carboxylic acids, amino acids and peptides, and inorganic acids such as phosphoric and sulfuric acids.

The present invention derives its principal advantages from the use of dibenzoxazepinone and dibenzothiazepinone chromogens as intermediates which are derivatized with an appropriate enzymatically-cleavable group Y. In particular, when the enzymatically-cleavable group Y is cleaved by a specific enzyme therefor in a basic solution, preferably from between about pH 7.0 to pH 10.0, a deprotonated form of the chromogen is liberated having an absorbance maximum which is substantially greater than the absorbance maximum of the chromogenic enzyme substrate compound of the present invention whereby a distinct change in absorbance therebetween is provided. The distinct change in absorbance provides a readily observable and detectable optical signal which can be accurately measured and correlated to the amount of enzyme present in a liquid test sample.

DESCRIPTION OF THE PREFERRED EMBODIMENTS

Figure 1:
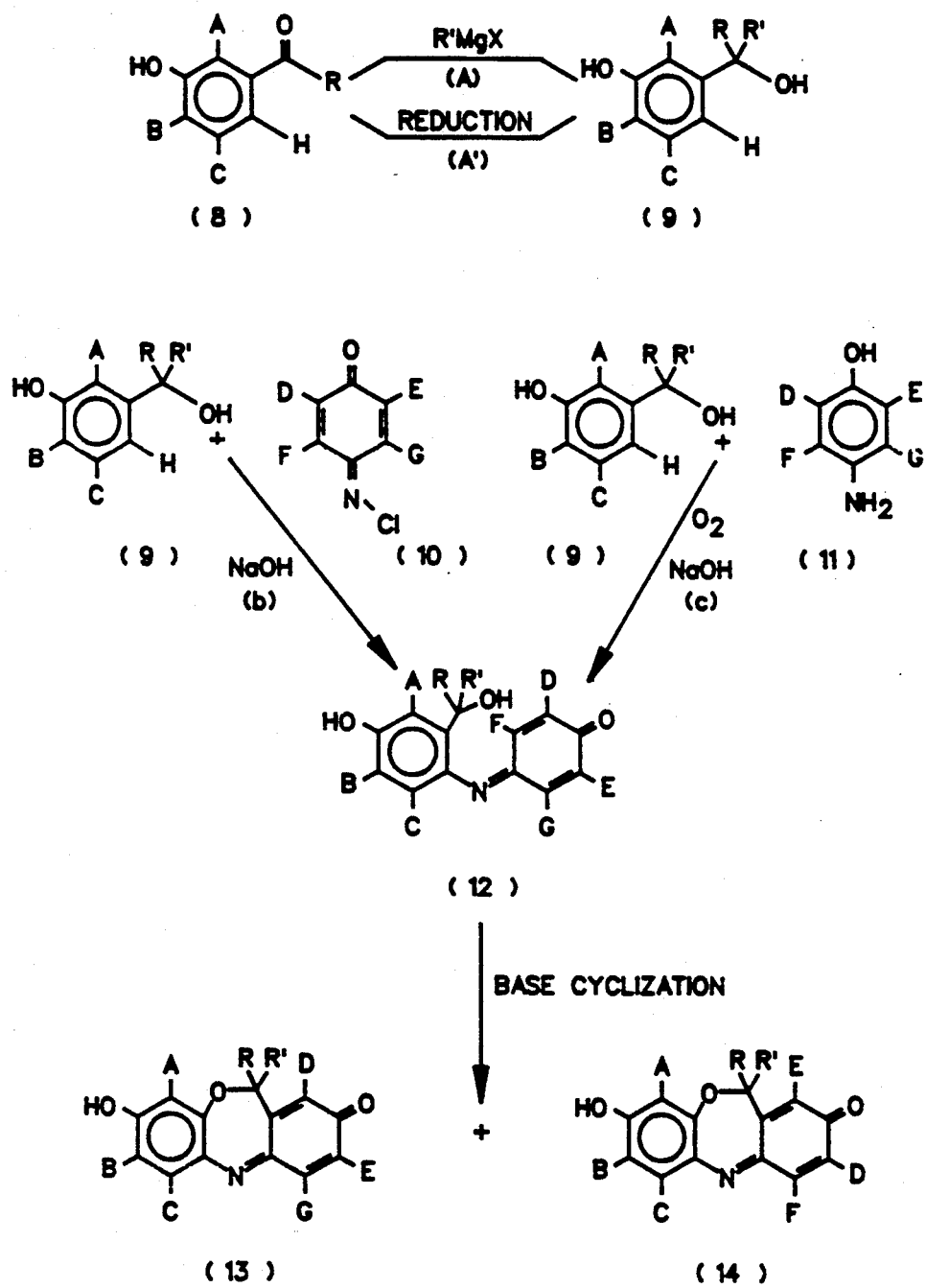
FIG. 1 is a flow diagram of the synthetic pathway for the preparation of 8-hydroxy-11H-dibenz[b,e][1,4]oxazepin-2-one chromogens.

The chromogenic enzyme substrate compounds of the present invention are derived from chromogens having the general formula:

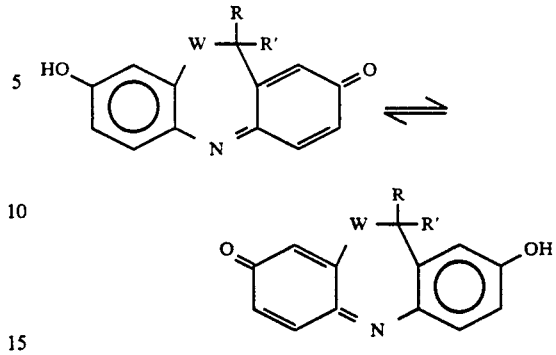

Where W is oxygen, the chromogen will be a mixture of the isomers 8-hydroxy-11H-dibenz[b,e][1,4]-oxazepine-2-one and 2-hydroxy-11H-dibenz[b,e][1,4]-oxazepine-8-one (such O-analog chromogens and their derivatives will be referred to herein as dibenzoxazepinones). Where W is sulfur, the chromogen will be a mixture of the isomers 8-hydroxy-11H-dibenzo[b,e][1,4]thiazepin-2-one and 2-hydroxy-11H-dibenzo[b,e][1,4]thiazepin-8-one (such S-analog chromogens and their derivatives will be referred to herein as dibenzothiazepinones). The dibenzazepinone where R is H and R' is methyl has been described in the literature [R. Hill, *Journal of Bioenergetics*, vol. 4, p. 229 (1973) and R. Hill, et al., *New Phytology*, vol. 77, p. 1 (1976)]. The visible absorption spectra of this chromogen has been described by T. Graan, et al., *Analytical Biochemistry*, vol. 144, p. 193 (1985), where a 122 nm shift in absorption ($\lambda_{max}$) between the protonated form and the deprotonated form of such chromogen was reported. Such deprotonation occurs in weakly acidic solutions, usually from between about pH 5.75 to pH 6.75, at the phenolic hydroxyl group of the chromogen by delocalization of the negative charge of the anion throughout the molecule. In the case of the present enzyme substrate compounds (1), enzymatic cleavage of the Y residue followed by deprotonization produces the chromogenic species:

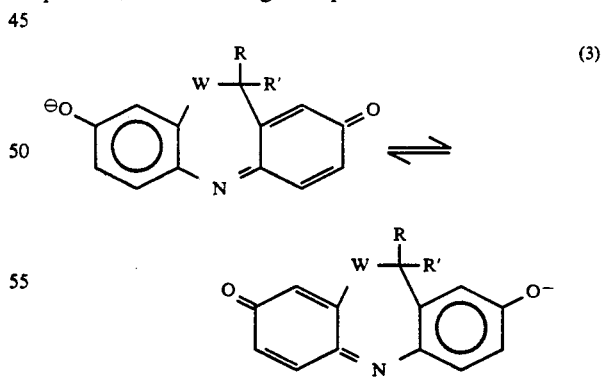

where W, R, and R' are as defined above.

According to the teachings of the present invention, when the phenolic hydroxyl group of the chromogen is derivatized with an enzymatically-cleavable group comprising a radical of a compound Y—OH which is an enzyme-specific moiety, the resulting compounds are novel isomeric chromogenic enzyme substrate compounds of the general isomeric formula:

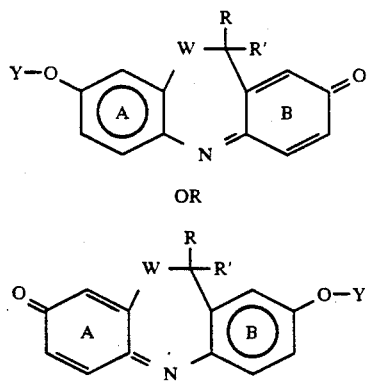

(4)

wherein Y represents the enzyme-cleavable group, and W, R, and R' are as defined above (hereinafter, references to compounds of the present invention by the use of only one of the two isomeric structures depicted in any of formulas (1) through (4) shall be understood to include reference to the other isomeric structure as well). The isomeric forms of the present substrate compounds can be used as a mixture, or can be separated by conventional means such as chromatography. The dibenzoxazepinones where W is O are particularly preferred. Moreover, it is preferred that R and R' be selected from H, lower alkyl, and phenyl, including substituted forms thereof. When one of R and R' is H or phenyl, it will generally be preferred that the other not also be H or phenyl, respectively. Particularly preferred are the dibenzoxazepinones (W=O) where R and R', same or different, are H or lower alkyl, especially where one of R and R' is H and the other is lower alkyl, e.g., methyl, or where both R and R' are methyl.

It should be understood that the present invention describes the first use of the dibenzoxazepinone and dibenzothiazepinone classes of chromogens as indicator groups in chromogenic enzyme substrates and, accordingly, encompass a wide variety of substituted dibenzoxazepinone and dibenzothiazepinone derivatives. It will be evident that the aromatic rings A and B in the formula (4) can bear a variety of substituent groups without departing from the scope of the present invention. As discussed in greater detail hereinafter, such substituent groups are limited only by the ability of one of ordinary skill in the art to prepare stable compounds which have the chromogenic enzyme substrate properties of the present invention, and include such groups as unsubstituted and substituted alkyl, unsubstituted and substituted aryl, alkoxy, aryloxy, halo (e.g., fluoro, chloro, bromo), nitro and substituted amino such as dialkylamino.

In the context of the present invention, "alkyl" is intended to include linear and branched forms of unsubstituted hydrocarbon residues of the general formula—$C_nH_{2n+1}$, preferably of the "lower alkyl" aliphatic type wherein n is 6 or less, such as methyl, ethyl, n-propyl, iso-propyl, n-butyl, iso-butyl, tert-butyl, n-hexyl, and the like, as well as substituted forms thereof.

Further, in the context of the present invention "aryl" is intended to include organic residues derived from an aromatic hydrocarbon ring or ring system by removal of a hydrogen atom, and include the unsubstituted hydrocarbon ring residues such as phenyl and napthyl, and substituted forms thereof. For purposes of the present invention, aryl residues include those bearing one or more same or different functional groups or substituents which can be selected by one skilled in the art to provide the chromogenic enzyme substrate compounds of the present invention.

More particularly, where "aryl" and "alkyl" are substituted, such substitution is intended to include such groups or substituents when mono- or polysubstituted with functional groups which do not substantially detract from the useful features of the present compounds. Such functional groups include chemical groups which may be introduced synthetically and result in the stable and useful chromogenic enzyme substrate indicator compounds of the present invention. Examples of such functional groups include, but are not intended to be limited to, halo (e.g., fluoro, chloro, bromo), substituted amino such as dialkylamino, nitro, alkoxy, aryloxy, alkyl, and aryl.

In particular, where R and/or R' are alkyl, preferably lower alkyl, such alkyl groups include, but are not intended to be limited to, methyl, ethyl, n-propyl, iso-propyl, n-butyl, iso-butyl, tert-butyl, n-hexyl, and substituted forms thereof including, but not necessarily limited to, benzyl, dialkylaminomethyl, more particularly dimethylaminomethyl, or halomethyl, more particularly bromomethyl, and the like. Where R and/or R' are aryl, such aryl groups include, but are not intended to be limited to, napthyl, phenyl, p-chlorophenyl, 2,4-dimethoxyphenyl, and the like.

The chromogenic enzyme substrate compounds (1) possess essentially the same color properties as the protonated form of the chromogen, regardless of the pH of the surrounding liquid environment, wherein upon contact of the derivatized chromogenic enzyme substrate compound (1) with an appropriate enzyme in a surrounding environment comprising a solution from between about pH 6.5 to pH 10, the enzymatically-cleavable group Y is cleaved by the enzyme to liberate the dissociated or deprotonated form of the chromogen (3) having an absorbance maximum which is substantially greater than the absorbance maximum of the chromogenic enzyme substrate compound to provide a distinct change in the absorbance maximum therebetween. Accordingly, the chromogenic enzyme substrate compounds of the present invention are particularly useful in an analytical test system which requires the detection of an enzyme-labeled assay reagent employed therein. The distinct and measurable change in the absorbance maximum which is generated between the substrate compound and the deprotonated form of the chromogen can be accurately detected, measured and correlated to the amount of analyte present in a liquid test sample.

Enzymatically-Cleavable Groups

According to the present invention, the enzyme-cleavable group Y is a radical of a compound Y—OH comprising an enzyme-specific moiety to provide novel chromogenic enzyme substrate compounds which confer specificity to a wide variety of enzymes encountered in analytical chemistry, particularly clinical chemistry, and particularly hydrolases. The compound Y—OH is intended to include, but is not necessarily limited to, sugars and derivatives thereof, acyl groups including aliphatic and aromatic carboxylic acids including amino acids and peptides, and inorganic acids such as phosphoric and sulfuric acid groups.

It is to be understood that it will be evident to one skilled in the art that the selection of the enzymatically-cleavable group Y will depend, of course, upon the particular enzyme of interest. For example, where the enzyme of interest is a glycosidase, a glycoside can be prepared in which the enzymatically-cleavable group Y is the glycosidic radical corresponding to the natural substrate for the particular glycosidase. Suitable glycosidic radicals include, but are not intended to be limited to, mono- and oligosaccharide radicals, which are capable of being incorporated into a glycoside substrate specific for a particular glycosidase enzyme and cleaved by said enzyme, such as radicals of β-D-galactopyranose, α-D-galactopyranose, β-D-glucopyranose, α-D-glucopyranose and α-D-mannopyranose, as well as amino sugars such as N-acetylglucosamine and N-acetylneuraminic acid, and the like radicals. Other suitable glycosidic radicals include oligosaccharide chains from between about 2 to 20, preferably 2 to 7, monosaccharide units attached by α-1-4 glucosidic linkages, which can be broken down by saccharide-chain splitting enzymes to a mono- or oligosaccharide which, in turn, can be cleaved by a corresponding glycosidase, such as, for example, radicals of maltopentose, maltohexose and maltoheptose.

It is to be understood that in some instances where the glycosidic radical is an oligosaccharide chain as heretofore described, such chain is first modified or broken down to a shorter oligosaccharide or monosaccharide by the enzyme under determination to produce a secondary substrate compound in which the enzymatically-cleavable group is cleaved from the nucleus of the substrate compound by a secondary enzyme, in which case the secondary substrate compound is then contacted with the secondary enzyme to generate a measurable change in absorbance as heretofore described. For example, where the enzyme under determination is α-amylase, the oligosaccharide chain is cleaved to produce a secondary glycoside substrate compound, e.g., an α-glucoside or β-glucoside, in which the resulting glycoside group thereof is cleavable from the nucleus of the substrate compound by a secondary glycosidase enzyme, e.g., α-glucosidase or β-glucosidase, respectively.

In the case of nonspecific esterase enzymes, the enzymatically-cleavable group Y is a radical of an acyl group to provide a chromogenic ester of the formula:

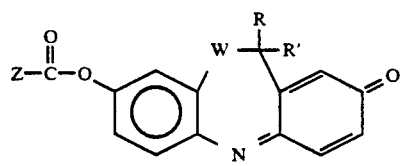

Where Z is lower alkyl or aryl, such compounds can be employed for the detection of nonspecific esterase enzymes such as cholinesterase, acylase, lipase, and the like. The chromogenic enzyme substrate compounds of the present invention can also be utilized for the detection of proteolytic enzymes commonly found in leukocytes. In such compounds is a radical of the compound Y—OH which is an N-protected amino acid or short peptide, e.g., consisting of between about 2 to 5 amino acid units. For example, Y can be a radical of the N-protected amino acid N-tosyl-L-alanine as represented by the formula:

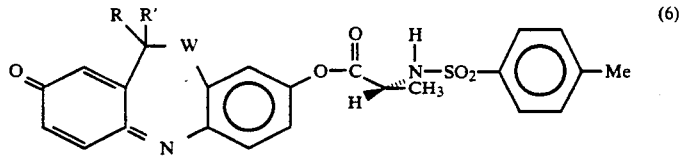

It will be appreciated that the present invention contemplates other carboxylic acid residues, amino acid residues and N-protecting groups as equivalents, as will be described in greater detail hereinafter.

Similarly, for the detection of alkaline phosphatase from a liquid test sample, the enzymatically-cleavable group Y is a radical of the compound Y—OH wherein Y—OH is a phosphoric acid group of the formula:

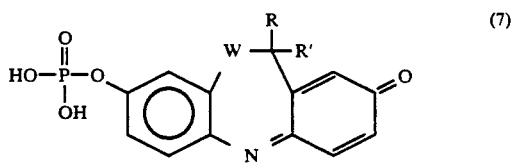

Preparation of Chromogenic Enzyme Substrate Compounds

The chromogenic enzyme substrate compounds (1) of the present invention can be prepared by reacting the compound Y—OH, where Y is a selected enzymatically cleavable group, with an appropriately derivatized dibenzoxazepinone or dibenzothiazepinone chromogen, as will be described in greater detail hereinafter, under condensation reaction conditions known in the art. Generally, the appropriate dibenzoxapeinone or dibenzothiazepinone chromogen is coupled under appropriate conditions with a reactive derivative of the compound Y—OH, preferably a carbohydrate (sugar) or carbohydrate-derivative or an acid as heretofore described, to provide a chromogenic enzyme substrate having the desired stereoisomerism.

As stated above, the present invention contemplates various substituents which can be substituted at the aromatic rings A and B of the nucleus shown in formula (4). Substituted equivalents are prepared through the use of appropriately derivatized dibenzoxazepinones or dibenzothiazepinones which can be prepared according to methods known in the art.

The preparation of dibenzoxazepinones (FIG. 1) employs, as starting materials, a 3-hydroxyacetophenone, a 3-hydroxybenzophenone or a 3-hydroxybenzaldehyde (8) and an appropriate Grignard reagent which are reacted [reaction (a)] to result in a substituted phenol (9). Alternately, the 3-hydroxyactophenone, 3-hydroxybenzophenone or 3-hydroxybenzaldehyde (8) may be reduced [reaction (a')] using an appropriate reducing agent. The phenol (9), in turn, is reacted [reaction (b)] with a substituted benzoquinone-N-chloroimine (10) to result in a functionalized indophenol (12). The indophenol (12) is then allowed to cyclize in base to result in the desired substrate compound (13 and 14).

In particular, the phenols (9) are prepared according to the method described by Hill, et al., supra, where R and R' can both be methyl or phenyl and A, B and C are hydrogen, from the corresponding 3-hydroxyacetophenone or 3-hydroxybenzophenone (8) which are reacted with [reaction (α)] a methylmagnesium bromide Grignard reagent or phenylmagnesium iodide Grignard reagent respectively. It is to be appreciated that the Grignard reagent can be selected from a wide variety of such reagents which have been described in the art and include, but are not necessarily limited to alkyl and aryl Grignard reagents, such as where X represents bromine or iodine, as well as those bearing functional group substituents such as -O-alkyl (alkoxy), -O-aryl (aryloxy), -alkyl and -aryl. Similarly, the synthesis of a variety of substituted 3-hydroxyacetophenones (8) where R can be alkyl or substituted alkyl, and 3-hydroxybenzophenones (8) where R can be aryl or substituted aryl, have been described and include compounds of the general formula (8) where R, A, B and C can be selected from a wide variety of substituents known in the art. For example, R can be methyl, A and C can be hydrogen, and B can be bromo, chloro, iodo, methyl or cyclohexyl [*J. Med. Chem.*, Vol. 23, p. 738(1980)]; or R and C can be methyl, A and B can be nitro and hydrogen or hydrogen and nitro, respectively, or A and B can be hydrogen [*Chem. Ber.*, Vol. 92, p. 2172(1959)]; or R can be methyl, A and C can be hydrogen, and B can be methoxy [*Chem. Ber.*, Vol. 55B, p. 1892(1922)] or cyclohexylether [*J. Chem. Soc.*, p. 3430(1951)]; or R and A can be methyl, B can be hydrogen, and C can be nitro [*J. Org. Chem.*, Vol. 14, p. 397(1949)]; or R can be methyl, A and B can be methoxy, and C can be hydrogen [*J. Prakt. Chem.*, Vol. 103, p. 329(1922)]; or R can be methyl, A and C can be hydrogen, and B can be p-hydroxyphenol [*Hoppe-Seyler's Z. Physiol. Chem.*, Vol. 292, p. 58(1953)]; or A, B and C can be hydrogen, and R can be dimethylaminomethyl [*Monatsh.*, Vol. 80, p. 517(1949)]or benzyl or phenylethyl [*Medd. Norsk. Farm. Selskap.*, Vol. 24, p. 45(1962) or p-chlorophenyl [*J. Chem. Soc.*, p. 5(1946)] or 2,4-dimethoxyphenyl [*Bull. Soc., Chim. France*, p. 1682(1959)]; or R can be bromomethyl and where A, B or C is nitro, then B and C, A and C or A and B can be hydrogen, respectively [*Acta Univ. Szeged., Acta Phys. Chem.*, Vol. 9, p. 48(1963)]; or R can be phenyl and A and C can be hydrogen and B can be methyl [*Helv. Chim. Acta.*, Vol. 29, p. 1413(1946)]or A and B can be methoxy and C can be hydrogen [*J. Org. Chem.*, Vol. 24, p. 952(1959)]; and the like.

Phenols (9) in which either or both R and R' are H are prepared from the corresponding 3-hydroxybenzaldehyde, 3-hydroxyacetophenone or 3-hydroxybenzophenone (8) by reduction [reaction (α')] of the carbonyl group to a hydroxyl group using a variety of reducing agents. Such reducing agents are known in the art (see House, *Modern Synthetic Reactions*, 2nd edition, W. A. Benjamin, Inc., Menlo Park, Calif., 1972, pp. 1-227) and include lithium hydride, lithium aluminum hydride, sodium borohydride and catalytic hydrogenation.

The desired indophenol (12) is prepared by reacting the appropriately substituted phenol (9) resulting from reaction (α) or (α') with an appropriately substituted benzoquinone-N-chloroimine (10) in aqueous alkali [reaction (b)] as described by Hill, et al, supra, where all of A-G can be hydrogen, and as described more generally by Gibbs, et al., Supplement No. 69 to the *Public Health Reports*, Washington, D.C. (1928), where all of substituents D, E, F and G in the general structure (10) can all be hydrogen, or D can be methyl and E, F and G can be hydrogen, or D, E and G can be hydrogen and F can be methyl, or D and E can be chlorine or bromine and F and G can be hydrogen, respectively. An alternate synthetic pathway for the preparation of the indophenol (12) is also described by Corbett, *J. Chem. Soc.* (B), p. 1502 (1970) where an appropriately substituted phenol (9) is reacted with an appropriately substituted p-aminophenol (11) and oxygen in the presence of aqueous alkali [reaction (o)]. The substituents D, E, F and G of the p-aminophenol (11) are described where D, E and G can be hydrogen and F can be methyl or chlorine, or D, F and G can be hydrogen and E can be methyl, or D and G can be methyl and E and F can be hydrogen, or D and E can be methyl or chlorine and F and G can be hydrogen, or D can be chlorine and E, F and G can be hydrogen, respectively.

The indophenol (12) resulting from either reaction (b) or (c) is then employed to prepare the substrate compounds (13) and (14) according to the method described by Hill, et al., *New Phytology* vol. 77, page 1 (1976), [reaction (d)] where the indophenol (12) is cyclized (step 2) in aqueous base, preferably sodium borate (borax), for several days at ambient temperature. It is to be appreciated that it is not necessary to isolate the various intermediates resulting from steps 1-3 of reaction (d) to obtain satisfactory yields of the substrate compounds (13) and (14).

Figure 2:
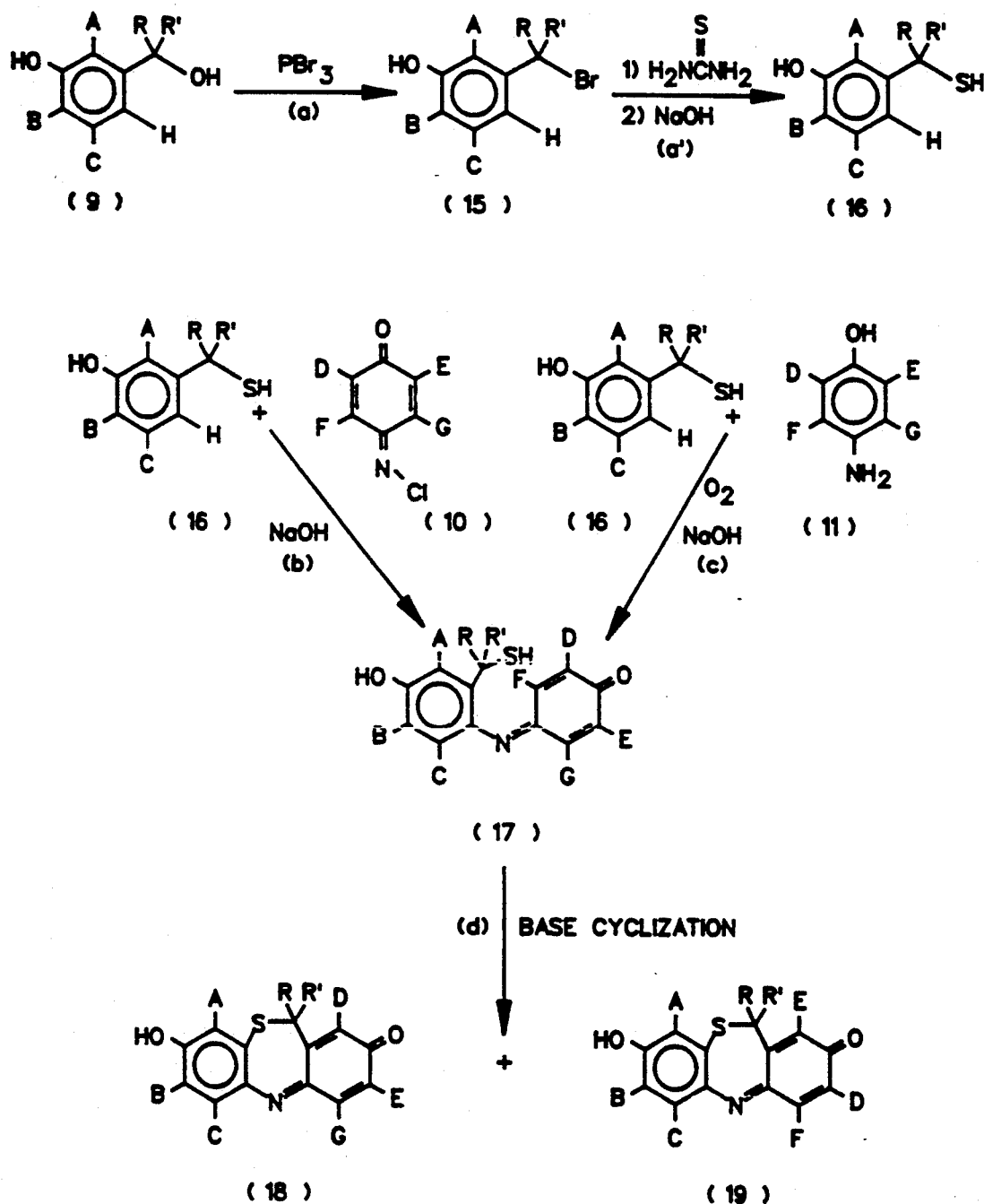
FIG. 2 is a flow diagram of the synthetic pathway for the preparation of 8-hydroxy-11H-dibenzo[b,e][1,4]thiazepin-2-one chromogens.
Figure 3:
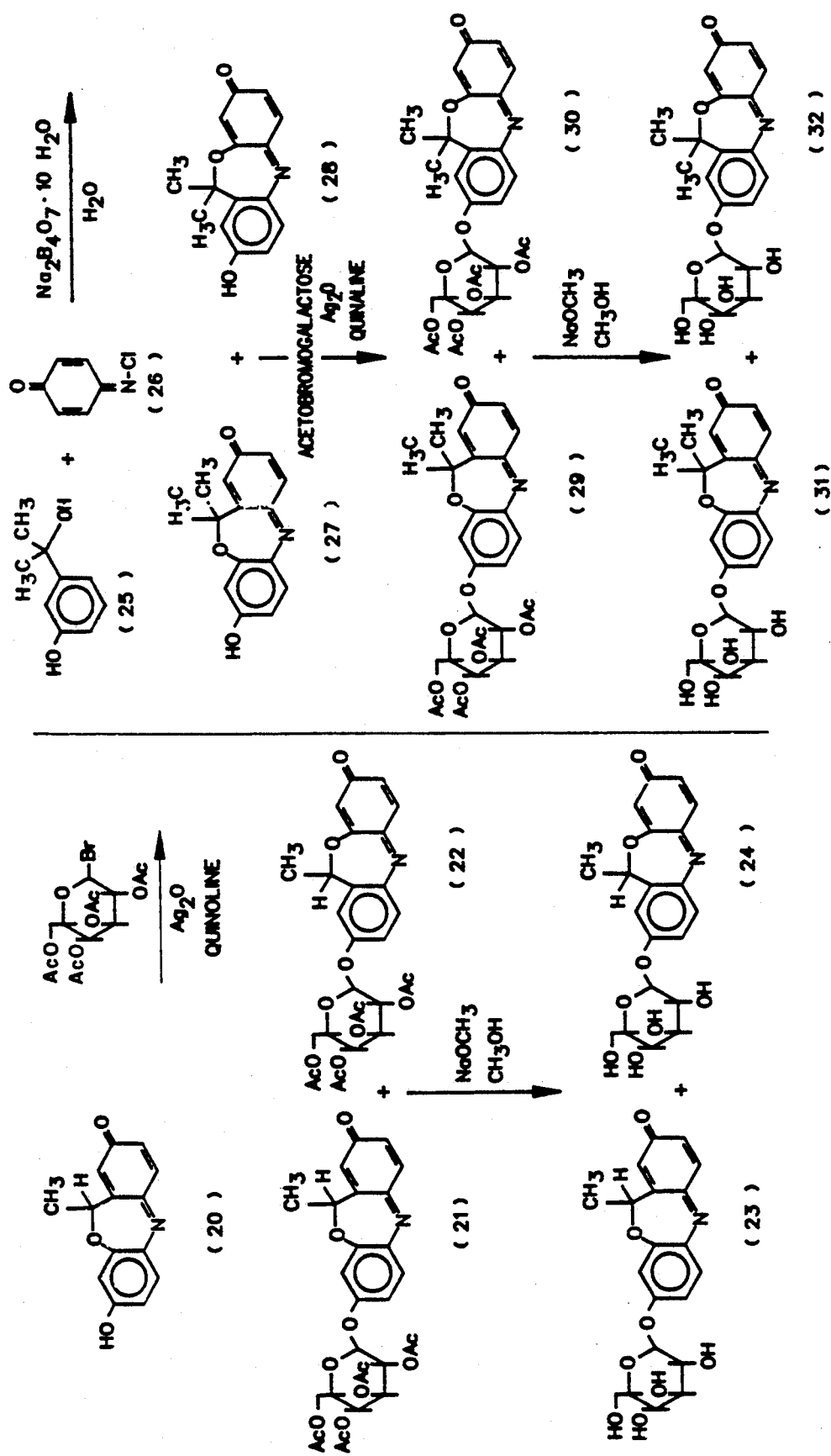
FIG. 3 is a flow diagram of the synthetic pathways for the preparation of chromogenic enzyme substrate compounds of the present invention.

The preparation of dibenzothiazepinones (FIG. 2) employs as starting materials substituted 3-mercaptomethylphenols (16) which are obtained from the previously described substituted 3-hydroxymethylphenols (9) via a two step process consisting of bromination [reaction (a)] to afford substituted 3-bromomethylphenols (15) followed by reaction with thiourea and base hydrolysis [reaction (a')]. The phenols (16) are in turn reacted [reaction (b)] with a substituted benzoquinone-N-chloroimine (10) to result in a functionalized indophenol (17). The indophenol (17) is then allowed to cyclize in base to result in the desired substrate compound (18 and 19).

In particular, the synthesis of 3-hydroxybenzyl bromide (15, R=R'=A=B=C=H) from 3-hydroxybenzyl alcohol (9, R=R'=A=B=C=H) is described in *J. Med. Chem.* vol. 23, p. 1013 (1980), and its conversion to 3-mercaptomethylphenol (16, R=R'=A=B=C=H) is reported in *J. Chem. Soc. Perkin 1.*, p. 1555 (1980). More generally, transformation of a variety of substituted 3-hydroxy-benzyl alcohols (9) to the corresponding 3-mercaptomethylphenols (16) with this procedure or with other appropriate procedures is within the ordinary skill in the art.

The specific nature of substituted benzoquinone-N-chloroimines (10) and substituted p-aminophenols (11) are the same as previously described, and the remaining steps (b), (c) and (d) are the same as those previously described for the dibenzoxazepinones (13 and 14).

It is to be appreciated that selection of appropriately derivatized starting materials and an appropriate Grignard reagent or reducing agent results in a variety of substituted phenols and, accordingly, one skilled in the art of organic chemical synthesis can prepare specific indophenols having a variety of substituents which can be converted to a desired appropriately derivatized dibenzoxazepinones and dibenzthiazepinones for use as the chromogen of the chromogenic acridinone enzyme substrate compounds of the present invention.

The glycoside derivatives of the general formula (1) can be prepared according to methods known in the art of carbohydrate chemistry employing known derivatives of carbohydrates of the formula Y—OH which are reacted with an appropriate chromogen. Such carbohydrate derivatives, which in some instances carry protecting groups, are commercially available (Aldrich Chemical Co., Milwaukee, Wis., USA; Sigma Chemical Co., St. Louis, Mo., USA), or can be prepared according to methods known in the art [*Methods in Carbohydrate Chemistry* (Academic Press, 1963), Vol. 2]. Glycosidic radicals include, but are not intended to be limited to, radicals of sugars such as $\beta$-D-galactopyranose, $\alpha$-D-galactopyranose, $\beta$-D-glucopyranose, $\alpha$-D-glucopyranose, $\alpha$-D-mannopyranose, N-acetylglucosamine, $\beta$-glucuronic acid and neuraminic acid. Other suitable glycosidic radicals include radicals of oligosaccharide chains which by saccharide-chain splitting enzymes can be broken down to the level of a mono- or oligosaccharide, which in its turn can be directly split off from the nucleus of the substrate compound with the corresponding glycosidase. It is to be understood that such oligosaccharide chains are chains consisting of from about 2 to about 20, preferably 2 to 7 monosaccharide units, such as maltopentose, maltohexose or maltoheptose. The chromogens of the general formula (2) are reacted with a mono- or oligosaccharide or a 1-halogeno-derivative thereof, where all hydroxyl groups are substituted with a protecting group according to methods known in the art of carbohydrate chemistry, to give per-O-substituted glycosides, from which the glycoside derivatives of general formula (1) are obtained by splitting off the protective groups according to methods known in the art.

The appropriate chromogens are reacted with the per-O-substituted 1-halogenosaccharides, preferably in the presence of proton acceptors such as alkali hydroxides or alkali carbonates, in aqueous acetone or (under phase transfer conditions) in a water/chloroform or water/benzene mixture. This procedure can furthermore be carried out by first converting the chromogens with alkali hydroxide or alcoholate into alkali salts or, using possibly substituted amines, into ammonium salts, and then reacting these with the per-O-substituted 1-halogeno saccharides in dipolar aprotic solvents such as acetone, dimethylsulfoxide, dichloromethane, tetrahydrofuran or dimethylformamide. Furthermore in the synthesis of per-O-substituted glycosides and per-O-substituted 1-halogenosaccharides, it is effective to use additives in the form of single silver salts or mixtures of silver salts, such as silver oxide, silver carbonate, silver carbonate on Celite® (Johns-Manville Corp., Denver, Colo., USA), silver triflate or silver salicylate, and/or of single mercury salts or mixtures of mercury salts, such as mercury bromide, mercury cyanide, mercury acetate or mercury oxide, and/or of single cadmium salts or mixtures of cadmium salts such as cadmium carbonate or cadmium oxide, possibly with the use of drying agents such as calcium chloride, a molecular seive or Drierite® (W. A. Hammond Drierite Co., Xenia, Ohio, USA), in solvents such as methylene chloride, chloroform, benzene, toluene, ethyl acetate, quinoline, tetrahydrofuran or dioxane. In the synthesis of $\alpha$-linked glycosides, the chromogen is melted with a saccharide whose hydroxy groups are substituted with a protective group, preferably an acetyl-group, in the presence of a Lewis acid, such as zinc chloride [see *Chem. Ber.* 66, 378–383 (1933) and *Methods in Carbohydrate Chemistry* (Academic Press, 1967) Vol. 2, pp. 345–347]. The temperature of the reaction is preferably between 80° and 130° C., more preferably between 110° and 130° C. The resulting per-O-substituted glycosides likewise are new compounds. Removing the protecting groups from the per-O-substituted glycosides to form glycosides is performed according to methods known in the art of carbohydrate chemistry [see *Advances in Carbohydrate Chem.* 12, 157 (1976)], such as with the protective acyl-groups with sodium methylate, barium methylate or ammonia in methanol. Suitable as a "protecting group" commonly used in carbohydrate chemistry is especially an acetyl, benzoyl, benzyl or trimethylsilyl-radical.

Derivatives of the general formula (1) where Y is the radical of an oligosaccharide chain of from about 2 to about 20 monosaccharide units attached via $\alpha$-1-4 glucosidic linkages can additionally be prepared from $\alpha$- and $\beta$-chromogen glucosides by an enzymatic process first described by French, et al., *J. Am. Chem. Soc.* 2387 (1954), and later by Wallenfels, et al., *Carbohydrate Research* 61, 359 (1978), involving the transfer of the glucoside to a pre-formed polysaccharide chain by the enzyme (1-4)-$\alpha$-glucan-4-glucosyltransferase (also known as cyclomaltodextrin glucanotransferase; EC 2.4.1.19).

Ester derivatives of the general formula (1) can be prepared by methods known in the art of organic chemistry by reacting an appropriate chromogen with known derivatives of carboxylic acids of the formula Y—OH, where Y=Z—C(O)— and where Z is defined the same as R and R' above. Such known derivatives of carboxylic acids of the formula Y—OH include, but are not intended to be limited to, amino acid residues, preferably residues of naturally-occurring $\alpha$-amino acids in their L- or D-form or also in their racemic form, the residues of glycine, alanine, valine, leucine, isoleucine, phenylalanine and tyrosine being preferred, the L-forms thereof being more preferred. Any free hydroxyl groups possibly present may be acylated and preferably acetylated. The peptide residues in this definition of Y—OH are to be understood to be, for example, amino acids or peptides from between about 2 to about 5 amino acid units such as di-, tri-, tetra-, and pentapeptides, di- and tripeptides being preferred, the amino acid components thereof being the above-mentioned amino acids. It is also to be understood that the amino groups of such amino acids or peptides may be protected with nitrogen protecting groups known in the art of peptide chemistry [see T. W. Green, *Protective Groups in Organic Synthesis* (J. Wiley and Sons, New York, N.Y., 1981), pp. 218–287] including, for example, acyl, oxycarbonyl, thiocarbonyl, sulphonyl, especially p-toluenesulphonyl (Tosyl, Ts), sulphenyl, vinyl, cyclohexenyl, and carbamoyl, especially t-butyl-(BOC) and benzyl-(CBz) carbamoyl radicals. Such esters may also be similarly prepared by reacting an appropriate chromogen with a carboxylic acid, amino acid or peptide, Y—OH as defined above, or with an appropriate reactive derivative thereof, employing methods known in the art of organic chemistry [see J. March, *Advanced Organic Chemistry: Reactions, Mechanism and Structure* (McGraw-Hill Book Co., New York, N.Y., 1968) pp. 319–323]. The reactive derivatives used can be, for example, acid chlorides or bromides, or mixed anhydrides conventionally used in peptide synthesis, such as those with ethyl chloroformate, or active esters such as those of N-hydroxysuccinimide.

Similarly, inorganic esters of the general formula (1) can be prepared according to methods known in the art of organic synthesis. The known derivatives of inorganic acids Y—OH, such as phosphoric acid or sulfuric acid are reacted with the chromogen employing methods known in the art of organic chemistry, such as shown in Koller and Wolfbeis, *Monatsh.* 116, 65 (1985) for inorganic esters of certain coumarins.

Analytical Test Systems

The chromogenic enzyme substrate compounds of the present invention are useful in analytical test systems which require the measurement of the amount of enzyme present therein, particularly those analytical test systems employing enzyme-labeled assay reagents. Such analytical test systems include, but are not intended to be limited to, enzyme immunoassays known in the art as competitive, sandwich and immunometric techniques where the amount of enzyme label in a particular fraction thereof can be measured and correlated to the amount of analyte under determination obtained from a liquid test sample.

The use of specific binding substances, such as antigens, haptens, antibodies, lectins, receptors, avidin, and other binding proteins, and polynucleotides, labeled with an enzyme have been recently developed and applied to the measurement of substances in biological fluids (see, for example, *Clin. Chem.*, Vol. 22, p. 1232 (1976); U.S. Reissue U.S. Pat. No. 31,006; and U.K. Patent No. 2,019,308). Generally, such measurement depends upon the ability of a binding substance, e.g., an antibody or an antigen, to bind to a specific analyte wherein a labeled reagent comprising such binding substance labeled with an enzyme is employed to determine the extent of such binding. Typically, the extent of binding is determined by measuring the amount of enzyme label present in the labeled reagent which either has or has not participated in a binding reaction with the analyte, wherein the amount of enzyme detected and measured can be correlated to the amount of analyte present in a liquid test sample.

The chromogenic enzyme substrate compounds of the present invention are particularly useful in analytical test systems as heretofore described where an analytical test device comprising a carrier matrix incorporated with the chromogenic enzyme substrate compound of the present invention is employed, the nature of the enzyme-specific moiety thereof depending, of course, upon the particular enzyme being detected.

The nature of the material of such carrier matrix can be of any substance capable of being incorporated with the chromogenic enzyme substrate compound of the present invention, such as those utilized for reagent strips for solution analysis. For example, U.S. Pat. No. 3,846,247 describes the use of felt, porous ceramic strips, and woven or matted glass fibers. As substitutes for paper, U.S. Pat. No. 3,552,928 describes the use of wood sticks, cloth, sponge material, and argilaceous substances. The use of synthetic resin fleeces and glass fiber felts in place of paper is suggested in British Pat. No. 1,369,139, and British Pat. No. 1,349,623 teaches the use of a light-permeable meshwork of thin filaments as a cover for an underlying paper matrix. This reference also teaches impregnating the paper with part of a reagent system and impregnating the meshwork with other potentially incompatible reagents. French Pat. No. 2,170,397 describes the use of carrier matrices having greater than 50% polyamide fibers therein. Another approach to carrier matrices is described in U.S. Pat. No. 4,046,513 wherein the concept of printing reagents onto a suitable carrier matrix is employed. U.S. Pat. No. 4,046,514 describes the interweaving or knitting of filaments bearing reagents in a reactant system. All such carrier matrix concepts can be employed in the present invention, as can others. Preferably, the carrier matrix comprises a bibulous material, such as filter paper, whereby a solution of the chromogenic enzyme substrate compound of the present invention is employed to impregnate the matrix. It can also comprise a system which physically entraps the assay reagents, such as polymeric microcapsules, which then rupture upon contact with the test sample. It can comprise a system wherein the assay reagents are homogeneously combined with the carrier matrix in a fluid or semi-fluid state, which later hardens or sets, thereby entrapping the assay reagents.

In a preferred embodiment, the carrier matrix is a bibulous material in the form of a zone or layer incorporated with the chromogenic enzyme substrate compound of the present invention which is employed where a particular assay is performed in a liquid environment employing an insoluble assay reagent known in the art to physically separate the free species of the labeled reagent from the bound species of the labeled reagent. According to such assay system, an aliquot of liquid containing the free species is removed and applied to the carrier matrix wherein the chromogenic enzyme substrate compound incorporated therein interacts with the enzyme label of the labeled reagent of the free species from the liquid test sample to provide a detectable signal which can be visibly observed and/or measured with an appropriate instrument, such as a spectrophotometer.

Similarly, a test device comprising two or more carrier matrices in the form of, for example, an uppermost layer or zone and a lowermost layer or zone can be employed. The lowermost layer of such test device can be incorporated with the chromogenic enzyme substrate compound of the present invention wherein a liquid test sample containing analyte under determination is applied to the uppermost layer of the device. The analyte which diffuses therein participates in the necessary binding reactions to generate a free and bound (i.e., immobilized) species of the enzyme labeled reagent therein as heretoforedescribed. Accordingly, the free species of the labeled reagent so generated is free to migrate into the lowermost layer where the enzyme label of the free species cleaves the enzymatically-cleavable group of the chromogenic enzyme substrate compound of the present invention incorporated therein to provide a measurable, detectable signal as heretofore described.

The present invention will now be illustrated, but is not intended to be limited, by the following examples. Italicised numbers in parenthesis refer to the structural formulae as used in the figures and/or the specification.

EXAMPLES

8-(Tetra-O-acetyl-β-D-galactopyranosyloxy)-11-methyl-11H-dibenz[b,e][1,4]oxazepin-2-one (21) and 2-(Tetra-O-acetyl-β-D-galacto TM pyranosyloxy)-11-methyl-11H-dibenz[b,f][1,4]-oxazepin-8-one (22)

A mixture of 8-hydroxy-11-methyl-11H-dibenz[b,e]1,4]oxazepin-2-one ("methyl purple") (20) (0.2 g; 0.83 mmol), prepared according to the method of Hill, et al, supra, acetobromogalactose (Sigma Chemical Co., St. Louis, Mo. USA) (0.685 g; 1.66 mmol) and silver (I) oxide ($Ag_2O$) (Aldrich Chemical Co., Milwaukee, Wis. USA) (0.425 g; 1.66 mmol) was stirred at ambient temperature in anhydrous quinoline (6.25 mL) and ethyl acetate (EtOAc) (2 mL) for 16 hours in a stoppered flask protected from light. The reaction mixture was diluted into EtOAc (approximately 40 mL), filtered through Celite (Johns-Manville Corp., Denver, Colo. USA) and extracted with small portions of 1M HCl until the extracts were acidic (pH=1). The combined aqueous extracts were washed with EtOAc (25 mL), then the combined EtOAc layers were washed with brine (20 mL), dried with sodium sulfate ($Na_2SO_4$), filtered and evaporated to dryness in vacuo to give a golden-yellow foam (0.8 g). The crude product was chromatographed on silica gel (100 g) using 7.5% (v:v) acetone in chloroform solvent and the two bright yellow product bands (Rf=0.28 and 0.34 on silica gel plates developed with acetone:chloroform [1:9]) were collected, combined, and freed of solvent to give a mixture of the title compounds as an orange foam (9.44 g; 92%).

IR (KBr) cm$^{-1}$ 2985, 1756, 1641, 1618, 1575, 1511, 1437, 1372, 1230, 1075.

$^1$H NMR (DMSO-d$^6$)δ: 1.4–1.7 (m, 3H), 1.9–2.2 (m, 12 H), 4.0–4.2 (m, 2 H), 4.45–4.55 (m, 1 H), 5.1–5.4 (m, 4 H), 5.6–5.76 (m, 1 H), 5.85–5.9 (m, 1 H), 6.4–7.7 (m, 5 H).

$^{13}$C NMR (DMSO-d$^6$) ppm. 187.93, 187.51, 169.99, 169.93, 169.59, 169.27, 159.48, 158.56, 157.73, 151.67, 144.71, 142.38, 142.00, 140.69, 137.00, 136.48, 134.34, 134.11, 130.51, 130.16, 125.75, 125.64, 116.69, 116.63, 113.04, 112.95, 110.99, 107.38, 96.94, 76.72, 75.03, 70.76, 70.16, 68.19, 67.34, 61.59, 20.52, 17.62, 17.23 (17 coincident bands).

Analysis: Calculated for $C_{28}H_{29}NO_{12}$:
C, 58.84; H, 5.11; N, 2.45;
Found: C, 58.61; H, 5.31; N, 2.29.

8-β-D-Galactopyranosyloxy-11-methyl-11H-dibenz[b,e][1,4]oxazepin-1-one (23) and 2-β-D-galactopyranosyloxy-11-methyl-11H-dibenz[b,e]-1,4]oxazepin-8-one (24)

A solution of (21) and (22) (0.41 g; 0.72 mmol) in HPLC grade methanol (25 mL) was treated at ambient temperature with sodium methoxide (31 mg) and allowed to stir for 1.5 hours. The reaction was quenched by addition of acetic acid (approximately 25 μL) then evaporated to dryness in vacuo to give an orange solid. The crude product was chromatographed on silica gel (100 g) using 15% (v:v) methanol in chloroform solvent and the bright orange product band (Rf=0.25 on silica gel plates developed with methanol: chloroform [1.4]) was collected and freed of solvent in vacuo to give a mixture of the title compounds as a red-orange solid. Vacuum drying for 2 hours at 64° C. gave the analytical sample (0.195 g; 67%).

IR (KBr) cm$^{-1}$ 3328, 2925, 2876, 1639, 1612, 1571, 1508, 1384, 1245, 1219, 1085, 896, 880, 823, 791.

$^1$H NMR (DMSO-d$^6$)δ: 1.4–1.7 (m, 3 H), 3.3–3.75 (m, 7 H), 4.5–4.75 (m, 5 H), 5.85–5.90 (m, 1 H), 6.4–7.65 (m, 5 H).

$^{13}$C NMR (DMSO-d$^6$) ppm. 187.95, 187.51, 161.18, 159.34, 158.67, 152.07, 151.61, 151.00, 144.76, 142.52, 142.11, 140.06, 136.96, 136.36, 134.28, 133.85, 130.31, 129.95, 125.00, 116.93, 116.84, 113.08, 113.04, 110.91, 107.36, 100.76, 100.59, 76.65, 75.94, 75.18, 73.34, 73.24, 70.21, 68.27, 68.19, 60.52, 60.44, 17.68, 17.30 (1 coincident band).

Analysis: Calculated for $C_{20}H_{21}NO_8$:
C, 59.55; H, 5.25; N, 3.47;
Found: C, 59.57; H, 5.48; N, 3.21.

When dissolved in 50 mM phosphate buffer at pH 7.4 containing 5 mM magnesium chloride ($MgCl_2$) compound (23)+(24) (mixture) had $\lambda_{max}$ of 454 nm ($\epsilon$=22,000) and 344 nm ($\epsilon$=14,000). In the presence of β-galactosidase, the substrate was cleaved to (20) at a rate ($K_{cat}$) of $1.32 \times 10^4$ mol. min$^{-1}$/mol. active site and exhibited a $K_m$ of 0.075 mM.

8-Hydroxy-11,11-dimethyl-11H-dibenz[b,e][1,4]oxazepin-2-one (27) and 2-hydroxy-11,11-dimethyl-11H-dibenz[b,e][1,4]oxazepin-8-one (28).

A solution of 2-(3'-hydroxyphenyl)-1-propanol (25) (2.20 g; 14.45 mmol) (prepared as described by Bruce, et al, J. Chem. Soc. (C), 1627 [1966]) and $Na_2B_4O_2 \cdot 10H_2O$ (borax) (28 g; 73.42 mmol) in $H_2O$ (200 mL) maintained at ambient temperature was treated with benzoquinonechloroimide (26) (2.0 g; 14.13 mmol) (prepared as described by Gibbs, et al, Supplement No. 69 to The Public Health Reports, Washington, D.C. [1928]) and tetrahydrofuran (5 mL), then allowed to stir for 7 days. The reaction was then acidified with 1M HCl and extracted four times with EtOAc (125 mL). The combined EtOAc layers were washed with brine (100 mL), dried ($Na_2SO_4$), filtered and evaporated to dryness in vacuo. The residue was chromatographed on silica gel (200 g) using acetone:chloroform (1:9) solvent; the red product band ($R_f$=0.33) was collected and freed of solvent in vacuo to give a mixture of the title compounds as a red powder (72 mg).

IR (KBr) cm$^{-1}$ 1634, 1614, 1556, 1311, 1213, 1180, 878.

$^1$H NMR (DMSO-d$^6$/ambient temperature)δ: 1.52 (br.s, 6 H), 5.8–7.7 (v.br.m, 6 H), 10.75 (br.s, 1 H).

$^1$H NMR (DMSO-d$^6$/100° C.)δ: 1.53 (s, 6 H), 2.98 (v.br.s, 1 H) (OH), 6.13 (br.s, 1 H), 6.57 (br.d, J=9.3 Hz, 1 H), 6.66 (br.s, 1 H), 6.73 (v.br.d., J=9.1 Hz, 1 H), 7.28 (d, J=9.3 Hz, 1 H), 7.44 (d, J=9.0 Hz, 1 H).

EIMS, m/e (relative intensity) 255 (M+, base), 240 (14.8), 226 (44.3), 212 (41.8), 210 (23.7), 198 (26.8), 184 (30.3).

Analysis: Calculated for $C_{15}H_{13}NO_3 \cdot 1/4 H_2O$:
C, 69.35; H, 5.24; N, 5.39;
Found: C, 69.54; H, 5.26; N, 5.38.

8-(Tetra-O-acetyl-β-D-galactopyranosyloxy)-11,11-dimethyl-11H-dibenz[b,e][1,4]oxazepin-2-one (29) and 2-(Tetra-O-acetyl-β-D-galactopyranosyloxy)-11,11-dimethyl-11H-dibenz[b,e][1,4]oxazepin-8-one (30).

A mixture of (27) and (28) (0.103 g; 0.4 mmol), acetobromogalactose (0.333 g; 2 eq) and silver (I) oxide ($Ag_2O$) (0.188 g; 2 eq) was stirred at ambient temperature in anhydrous quinoline (7 mL) and EtOAc (2 mL)

for 18 hours in a stoppered flask protected from light. The reaction mixture was diluted with EtOAc (approximately 40 mL), filtered through Celite and extracted three times with 1.0M HCl (30 ml each). The combined aqueous extracts were washed with EtOAc (40 mL) then the combined EtOAc layers were washed with brine (40 mL), dried ($Na_2SO_4$), filtered and evaporated to dryness in vacuo. The crude product was chromatographed on silica gel (93 g) using acetone:chloroform (7:93) solvent and the two yellow product bands ($R_f$=0.38 and 0.43 on silica gel plates developed with acetone:chloroform [1:9]) were collected, combined, and freed of solvent in vacuo to give a mixture of the title compounds as an orange foam (0.216 g; 92%).

IR(KBr)cm$^{-1}$ 1750, 1640, 1615, 1573, 1368, 1260, 1070, 955, 898.

$^1$H NMR (CDCl$_3$)δ: 1.45–1.70 (m, 6 H), 2.0–2.2 (m, 12 H), 4.08–4.26 (m, 3 H), 5.10–5.20 (m, 2 H), 5.45–5.55 (m, 2 H), 6.00–7.70 (m, 6 H).

$^{13}$C NMR (CDCl$_3$) ppm. 188.82, 188.50, 170.25, 170.04, 169.94, 169.26, 159.91, 158.00, 156.55, 151.67, 151.63, 150.56, 146.45, 145.38, 141.78, 140.19, 137.11, 136.59, 135.11, 130.70, 129.46, 129.31, 126.22, 124.96, 155.33, 115.28, 113.81, 112.76, 109.03, 98.54, 98.42, 80.14, 79.78, 71.29, 70.57, 68.32, 66.73, 61.42, 26.44, 26.23, 20.56 (17 coincident bands).

8-β-D-Galactopyranosyloxy-11,11-dimethyl-11H-dibenz[b,e][1,4]-oxazepin-2-one (31) and 2-β-D-galactopyranosyloxy-11,11-dimethyl-11H-dibenz[b,f][1,4]oxazepin-8-one (32).

A solution of (29) and (30) (0.21 g; 0.358 mmol) in HPLC grade methanol (20 mL) was treated at ambient temperature with sodium methoxide (22 mg) and allowed to stir for several hours. The reaction was quenched by addition of acetic acid (23 μL) then evaporated to dryness in vacuo. The crude product was chromatographed on silica gel (60 g) using methanol:chloroform (15:85) solvent and the orange product band ($R_f$=0.23 on silica gel plates developed with methanol:chloroform [1:4]) was collected and freed of solvent in vacuo to give the title compound as a red-orange powder (0.12 g; 80%).

IR(KBr)cm$^{-1}$ 3416, 2926, 1634, 1612, 1567, 1503, 1385, 1292, 1227, 1074, 889.

$^1$H NMR (DMSO-d$^6$)δ:1.45–1.65 (m, 6 H), 3.30–3.75 (m, 6 H), 4.5 (v.br.d, J=1.4 Hz, 1 H), 4.68 (br.q., J=6.7 Hz, 1 H), 4.91 (v.br.s, 1 H), 4.99 (t, J=6.9 Hz, 1 H), 5.23 (v.br.s, 1 H), 5.9–7.7 (m, 6 H).

$^{13}$C NMR (DMSO-d$^6$) ppm. 187.91, 187.76, 161.47, 159.68, 156.35, 150.61, 150.48, 150.31, 146.25, 145.62, 141.99, 140.91, 138.65, 137.23, 136.20, 134.09, 130.33, 129.19, 124.75, 116.15, 114.69, 113.32, 113.01, 108.65, 100.58, 100.42, 80.72, 79.99, 76.00, 75.78, 73.30, 73.24, 70.19, 68.26, 68.17, 60.52, 60.38, 26.01 (4 coincident bands).

Analysis: Calculated for $C_{21}H_{23}NO_8 \cdot 1\frac{1}{2} H_2O$:
C, 56.75; H, 5.90; N, 3.15.
Found: C, 56.61; H, 5.82; N, 3.14.

Test Device

A test device sensitive to the presence of β-galactosidase in a test sample was prepared. The device comprised a small rectangular piece of filter paper mounted at one end of an oblong strip of polystyrene film. The paper was impregnated with various ingredients, including (23) and (24), a buffer and inorganic salt. A 2 inch wide strip of Whatman 54 filter paper was immersed in an aqueous solution containing the following:

0.6M NaEpps Buffer (pH=8.4)
4.0 mM $MgCl_2$

The paper was then dried overnight in air. Next the paper was immersed in a DMF solution containing:

15 mM (23)+(24)

The paper was then dried in air at 50°–80° C. A yellow test paper was obtained.

The piece of the dried, impregnated paper was cut into a rectangle measuring 0.1 inch×0.4 inch and mounted at one end of an axially oriented polystyrene strip measuring 0.1 inch×3.25 inch. Mounting the paper to the strip was achieved using double-stick double-faced adhesive (3M Company).

Figure 4:
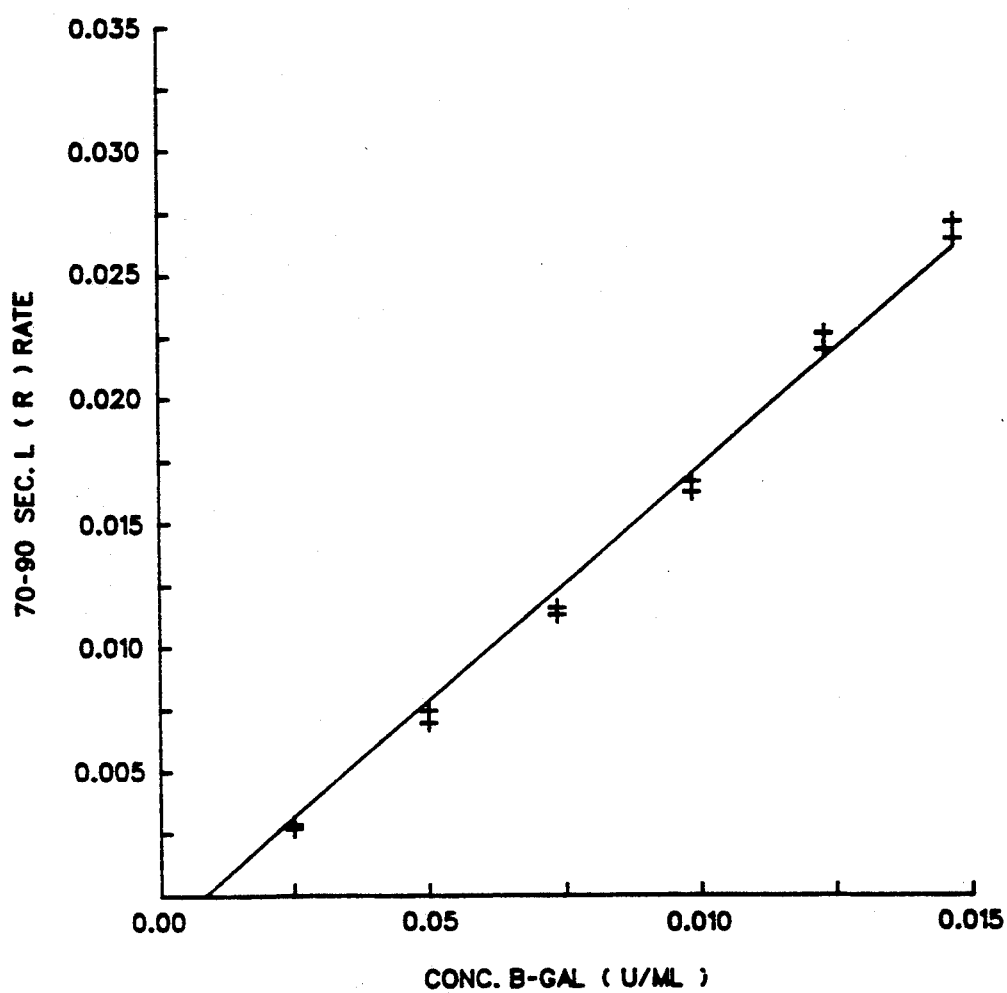
FIG. 4 is a graph which illustrates the dose response of a test device incorporated with the chromogenic enzyme substrate of the present invention to the presence of β-D-galactosidase.

Solutions of β-D-galactosidase in pH 6.4 potassium phosphate/citrate buffer were prepared at 0.025, 0.05, 0.075, 0.20, 0.125 and 0.15 IU/mL. Three analytical test devices were dipped into each test solution. The respective analytical test devices were then mounted in a SERALYZER ® Reflectance Photometer (Miles, Inc., Elkhart, Ind., USA) and the reflectance of light from the test device containing the liberated chromogen (20) was measured at 590 nm after 70–90 seconds wherein the reflectance values thereof were plotted against the respective test sample solution concentrations to reveal a linear dose response as exemplified in FIG. 4.

The present invention has been particularly described and exemplified above. Clearly, many other variations and modifications of the invention can be made without departing from the spirit and scope thereof.

What is claimed is:

1. A method for determining a particular enzyme in a liquid test sample, comprising the steps of:
   (a) contacting the test sample with a chromogenic enzyme substrate compound of the formula:

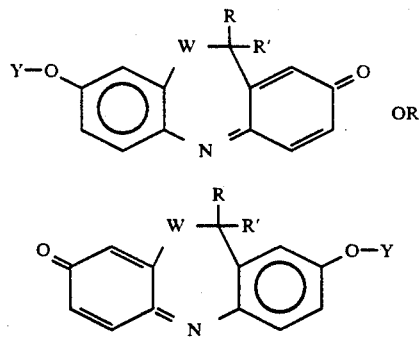

wherein W is O or S; R and R', which can be the same or different, are H, alkyl, or aryl; and Y is an enzyme-cleavable group that is
   (i) capable of being cleaved from the nucleus of the enzyme substrate compound by said enzyme, or
   (ii) capable of being modified by said enzyme to produce a secondary substrate compound in which Y is capable of being cleaved from the nucleus of the modified enzyme substrate compound by a secondary enzyme,
   and, in the latter case (ii), the secondary substrate compound is contacted with said secondary enzyme; and
   (b) measuring and correlating the resulting color generated by the cleaved nucleus of the enzyme substrate compound to the presence of said enzyme in said liquid test sample.

2. The method of claim 1 wherein said enzyme-cleavable group is a radical of a compound Y—OH comprising an enzyme-specific moiety selected from the group consisting of sugars and derivatives thereof, aliphatic and aromatic carboxylic acids, and inorganic acids.

3. The method of claim 2 wherein W is O.

4. The method of claim 3 wherein R and R', which can be the same or different, are H, lower alkyl, or phenyl.

5. The method of claim 4 wherein R and R' are not both H or phenyl.

6. The method of claim 3 wherein one of R and R' is H and the other is lower alkyl.

7. The method of claim 3 wherein one of R and R' is H and the other is methyl.

8. The method of claim 3 wherein R and R' are both methyl.

9. The method of claim 1 wherein said enzyme is a glycosidase and Y is a radical of a sugar or derivative thereof selected from the group consisting of α-D-galactose, β-D-galactose, α-D-glucose, α-D-glucose, α-D-mannose, N-acetylglucosamine and N-acetylneuraminic acid.

10. The method of claim 1 wherein said enzyme is α-amylase and Y is a radical of an oligosaccharide chain of from between about 2 to about 20 monosaccharide units which is capable of being modified by α-amylase to produce a secondary glycoside substrate compound in which the resulting glycoside group is cleavable from the nucleus of the substrate compound by a secondary glycosidase enzyme, and wherein the secondary glycoside substrate compound is contacted with said secondary glycosidase enzyme.

11. The method of claim 10 wherein said oligosaccharide chain is maltoheptose.

12. The method of claim 10 wherein said resulting glycoside group is a glucoside and said secondary glycosidase enzyme is a glucosidase.

13. The method of claim 1 wherein said enzyme is β-D-galactosidase and Y is a β-D-galactose radical.

14. The method of claim 1 wherein said enzyme is β-D-glucosidase and Y is a β-D-glucose radical.

15. The method of claim 1 wherein said enzyme is a non-specific esterase and Y is a radical of an aliphatic or aromatic carboxylic acid.

16. The method of claim 1 wherein said enzyme is a proteolytic enzyme present in leukocytes and Y is a radical of a carboxylic acid comprising an N-protected amino acid or a peptide of from between about 2 to about 5 amino acid units.

17. The method of claim 16 wherein Y is an N-tosyl-L-alanine radical.

18. The method of claim 1 wherein said enzyme is alkaline phosphatase and Y is a phosphoric acid radical.

19. The method of claim 1 wherein said enzyme is sulfatase and Y is a sulfuric acid radical.

* * * * *